United States Patent [19]
Scharf

[11] Patent Number: 5,816,816
[45] Date of Patent: Oct. 6, 1998

[54] METHOD OF PRODUCING FIBER REINFORCED DENTAL POST AND RESULTING DENTAL POST

[76] Inventor: Jonathan Scharf, 364-A7 St. Andrews Rd., Glenmoore, Pa. 19343

[21] Appl. No.: 819,616

[22] Filed: Mar. 17, 1997

[51] Int. Cl.$^6$ ..................................................... A61C 5/08
[52] U.S. Cl. ........................... 433/220; 433/215; 433/224
[58] Field of Search ..................................... 433/221, 220, 433/81, 215, 180, 225, 226, 136, 224

[56] References Cited

U.S. PATENT DOCUMENTS

| | | | |
|---|---|---|---|
| 5,074,792 | 12/1991 | Bernadat | 433/220 |
| 5,098,304 | 3/1992 | Scharf | 433/215 |
| 5,102,332 | 4/1992 | Uthoff | 433/6 |
| 5,176,951 | 1/1993 | Rudo | 433/180 |
| 5,425,640 | 6/1995 | Scharf | 433/215 |
| 5,518,399 | 5/1996 | Sicurelli, Jr. et al. | 433/220 |
| 5,564,929 | 10/1996 | Alpert | 433/220 |

Primary Examiner—Cary E. O'Connor
Attorney, Agent, or Firm—Michael F. Petock, Esq.

[57] ABSTRACT

A method of producing a dental post for use in restoring or stabilizing one or more teeth includes the steps of creating a hole in a tooth and obtaining a woven hollow rope which is mounted over a mandrel and inserted into the hole. The mandrel is withdrawn and the hollow rope is filled with a core-paste material. In a presently preferred embodiment, the woven hollow rope is woven in the form of a braid and the mandrel is in the form of a hollow needle attached to a syringe. In the preferred embodiment, the hollow rope is provided with a closed end and the needle is withdrawn while simultaneously filling the hollow rope with a core-paste material. The invention includes a new use for hollow woven rope, which is preferably hollow braided rope, in the formation of non-metallic fiber reinforced posts for use in dental application varying from dental posts used to support cores in root canal procedures to providing structural support for bridges, pontics and the like. The invention further includes the dental post constructed of a hollow woven rope which is injected with a core-paste material.

49 Claims, 3 Drawing Sheets

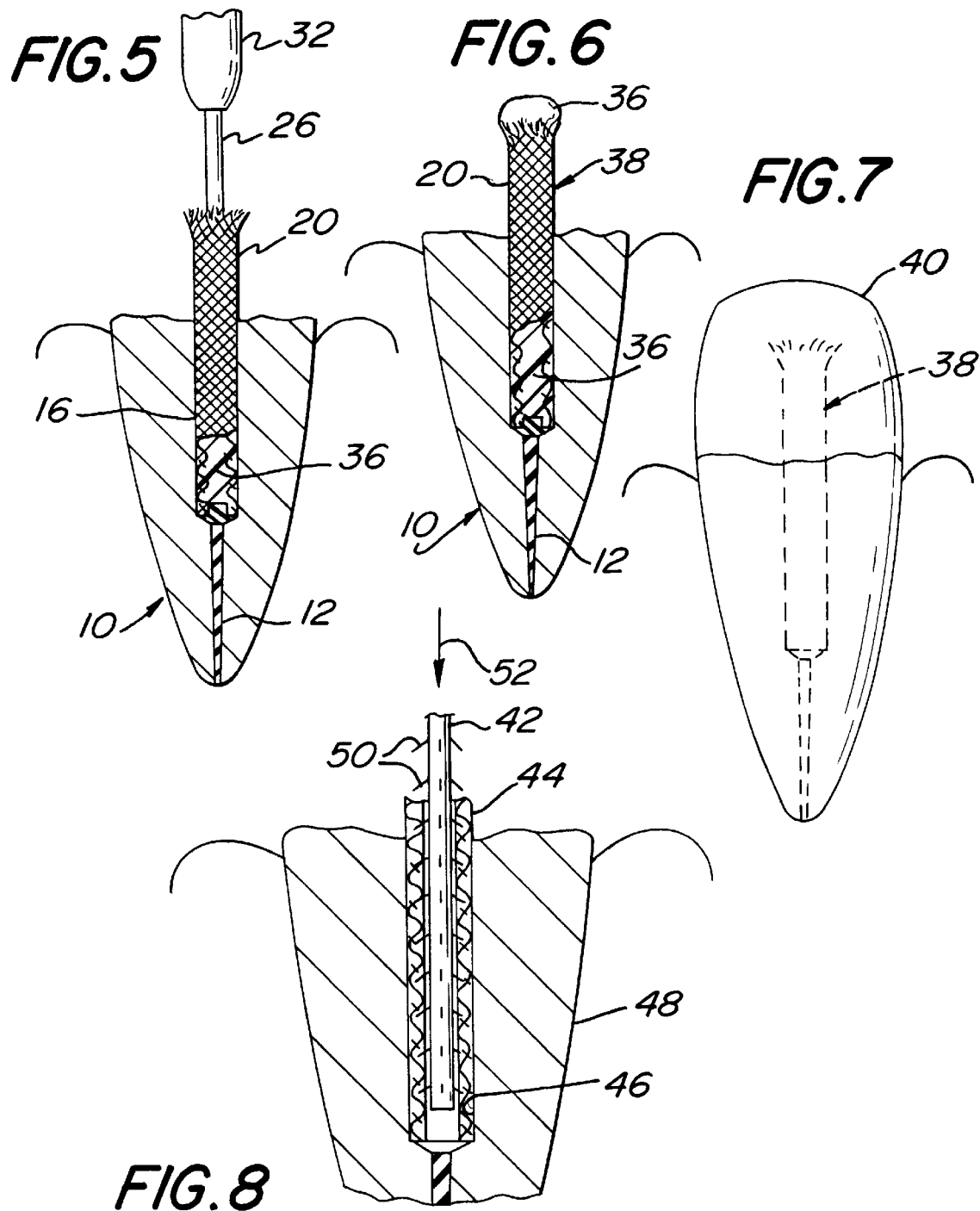

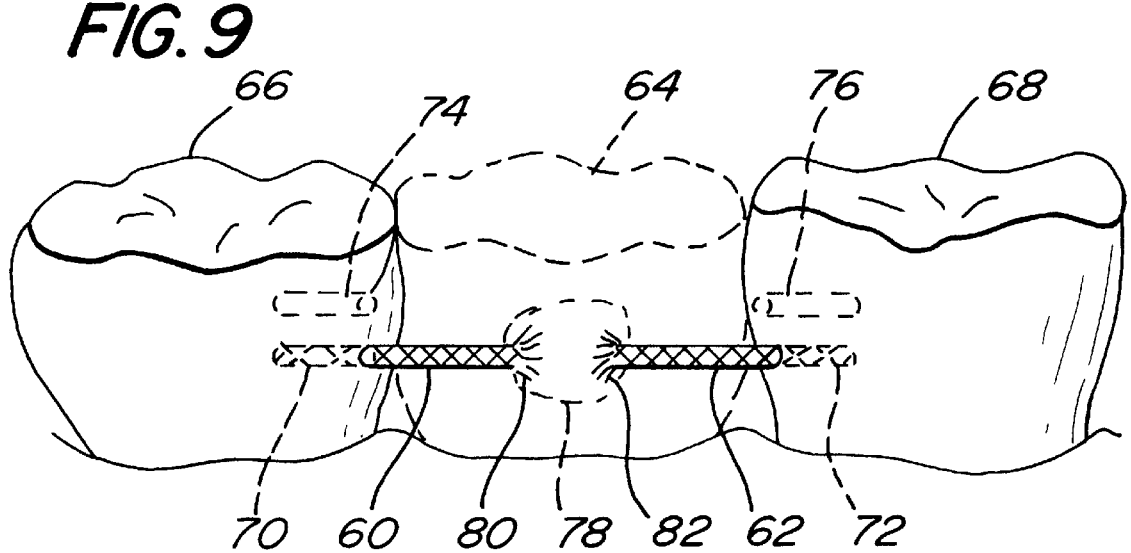

METHOD OF PRODUCING FIBER REINFORCED DENTAL POST AND RESULTING DENTAL POST

FIELD OF THE INVENTION

The present invention relates to a method of producing a fiber reinforced dental post and the resulting dental post. More particularly, the present invention relates to a new and unobvious method of utilizing a hollow woven rope as the reinforcing structure, a method of inserting the rope into a bore hole and creating the post, as well as variations on the method and various applications.

BACKGROUND OF THE INVENTION

Traditional methods of post placement in endodontically treated teeth utilizing laboratory-fabricated cast-metal or prefabricated metal screw-type posts have come under scrutiny due to the potential for root or tooth fracture resulting from excessive forces within the tooth.

In general, in the field of dentistry, in recent years, there has been an effort to move away from the use of metal in prosthetic and restorative dentistry, such as the movement away from gold crowns and other restorations of that type. However, with respect to posts, these have continued to be constructed of metal with their attendant disadvantages.

With respect to the use of fiber material as reinforcement in dentistry including ceramic and glass fiber ropes, meshes and tapes, including braided ropes, the inventor herein has made significant contributions as more fully described in his prior U.S. Pat. Nos. 5,098,304 and 5,425,640. The subject matter and teachings of those patents are incorporated herein by reference the same as if set forth at length. In those patents, various applications of ceramic and glass fiber material for use in reinforcing and strengthening various types of composite resins were described. Various reinforcement and stabilization applications of ceramic and glass fiber materials, including silanated ceramic and glass fiber material and etched and silanated ceramic and glass fiber materials, were disclosed, including the laying of ropes or tapes into channels cut into teeth. However, prior to the present invention herein, there was no known way of utilizing such glass fiber or other fiber materials to form dental posts for various applications as more fully described herein.

SUMMARY OF THE INVENTION

An advantage of the present invention is that it enables a new and improved construction of a dental post not of metal, but of a fiber reinforced material.

Another advantage of the present invention is that it enables complete and effective bonding to the tooth and to core-paste material which may be utilized to form the core for a crown or for the formation of a pontic or other structure.

Another advantage of the present invention is that it enables insertion of a reinforcing structure into a post hole formed in the tooth, such as subsequent to a root canal procedure.

Another advantage of the present invention is that it provides a procedure where the composite or acrylic core-paste material is injected directly into the reinforcing structure, which is a woven hollow rope.

Another advantage of the present invention is that the composite or acrylic core-paste utilized in forming the post completely wets the reinforcing fiber structure, wetting fiber structure from the internal direction outward and through or between the fibers to form a secure bond to the internal surface of the bore hole, that is, bonds to the tooth.

Another advantage to the present invention is that it adds to composite or acrylic mass in that it eliminates voids within the hollow rope structure which may serve as potential areas for failure of the structure.

Another advantage of the present invention is that it provides a convenient and effective means of delivering a flexible rope structure in a rigid form for insertion into a bore hole in a tooth such as may be required in the construction of a post in a root canal procedure or other reconstructive or stabilizing procedure.

Another advantage of the present invention is that it facilitates injection of composite or acrylic material internally after placement to gain the advantages as described above.

Briefly and basically, in accordance with the present invention, a method of producing a post hole for use in restoring or stabilizing one or more teeth which includes the steps of creating a hole in a tooth, obtaining a woven hollow rope and mounting the hollow rope over a mandrel. The mandrel with the hollow rope thereon is then inserted into the hole as a convenient means of delivering the rope into the hole. The mandrel is withdrawn and the hollow rope is filled with a core-paste material to form the dental post.

Preferably, the mandrel may be in the form of a hollow needle through which a core-paste material may be injected. Further, in a preferred embodiment, the woven hollow rope may be a braided hollow rope. In a presently preferred embodiment, the woven hollow rope may be provided with a closed end which may prevent the woven hollow rope from sliding on the needle during the insertion process, but other suitable mandrels may be used including a hollow or solid needle or rod with retaining means such as barbs thereon to hold the hollow rope in place on the mandrel during insertion.

The present invention includes the method of wetting a reinforcing structure by injecting a composite or acrylic material into the interior of a hollow woven rope wherein the composite or acrylic material may fill the inside and wet the reinforcing structure from the inside outwardly.

Further, the present invention includes a dental post constructed of a woven hollow rope utilized as the reinforcing structure which is then filled with a core-paste material. The core-paste material may be composite or acrylic and the woven hollow rope may be braided and comprised of any of the various fibers described herein, including ceramic or glass.

In a presently preferred method of practicing the invention, withdrawal of the needle may take place simultaneously with the filling of the hollow rope with a core-paste material. This enhances the ability to hold the supporting structure in the form of the hollow rope in place while the needle is being withdrawn. In accordance with the present invention, the woven hollow rope may be constructed of any suitable type of fiber material including ceramic fibers or glass fibers as well as silanated ceramic or glass fibers or etched and silanated ceramic or glass fibers. Other suitable fiber type materials may be utilized to construct the woven hollow rope.

The present invention further includes the new use for woven hollow rope, braided or otherwise, for creating dental posts by inserting them into a bore hole in a tooth and filling them with a core-paste material. Applications of the present method include the formation of posts in root canal procedures as well as any other procedure where another dental structure needs to be attached or supported by an adjacent tooth. A specific application is disclosed wherein one or more posts may be created in adjacent teeth to support another structure such as a pontic. Further, posts so created may be bonded together to provide more rigid support or a single reinforcing structure may be inserted into bore holes created in two separated teeth by creating the bore holes and then utilizing the procedure to insert one end of the reinforcing woven hollow rope into one of the bore holes. The mandrel or insertion needle is then utilized to insert the other end of the woven hollow rope into a second bore hole in the second tooth by passing it through an intermediate portion of the sidewall of the woven hollow rope. This may be done by making a slit in the sidewall of the woven hollow rope or by merely passing the needle between the fibers or strands of which the woven hollow rope is constructed. The procedures for insertion into each bore hole are similar to those described above.

Various other applications will be apparent to those skilled in the art.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 5 is an elevation view, partially in cross-section, showing the partial withdrawal of the needle and partial filling of the hollow rope with core-paste material.

FIG. 6 is an elevation view, partially in cross-section, of a dental post formed in the tooth.

FIG. 7 is an elevation view, showing in dotted outline the dental post, over which a core has been formed in preparation for a crown.

FIG. 8 is an elevation view, partially in cross-section showing an alternate form of a mandrel for insertion of the woven hollow rope into a bore hole formed in a tooth.

FIG. 9 is an elevation view showing the formation of a plurality of posts in separated teeth and, in dotted outline, the formation of a pontic thereon.

FIG. 10 is an elevation view illustrating a method of forming a post by insertion of opposite ends into two different separated teeth in accordance with the present invention.

DETAILED DESCRIPTION OF THE PREFERRED EMBODIMENTS

Figure 1:
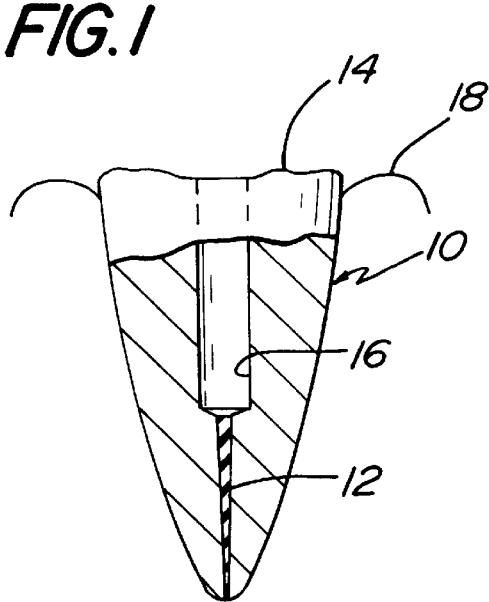
FIG. 1 is a cross-sectional view of a tooth having been prepared with a bore hole in preparation for a dental post after a root canal procedure.

Referring now to the drawings, wherein like numerals indicate like elements, there is shown in FIG. 1 a tooth 10 of which most of the coronal portion of the tooth is missing. A coronal portion of the tooth 10 may be missing because of traumatic injury, decay or for any other reason. Most of the remaining portion of tooth 10 is referred to as the root.

As illustrated in FIG. 1, tooth 10 is a tooth on which a root canal procedure has previously been performed wherein the nerve of tooth 10 has been removed and gutta percha material 12 has been placed in the root canal. The gutta percha material 12 would originally extend to the upper surface 14 of the remaining portion of tooth 10. Upper surface 14 in this case happens to be just above gum line 18. As illustrated in FIG. 1, tooth 10 has been prepared for the placement of a dental post by drilling or reaming out the gutta percha material to form a bore hole or post hole 16.

In accordance with the method and other aspects of the present invention, a dental post may be formed in a tooth utilizing a woven hollow rope material which may be inserted into a bore hole formed by a drill, reamer or the like and which is filled with a core-paste material. The woven hollow rope may be comprised of any suitable fibers including ceramic or glass fibers. Ceramic or glass fibers may be silanated or etched and silanated. Furthermore, other types of fibers may be utilized including silk or other suitable materials. Further, in a preferred embodiment of the present invention, the woven nature of the hollow rope is that of a braided material. In other words, in accordance with a presently preferred form of practicing the invention, the woven hollow rope would be comprised of a braided etched and silanated glass fiber. Such a braided construction provides expandability and contractibility of the diameter of the hollow woven rope and more easily conforms to the shape of the hole. In other words, such a braided construction may provide limited expandability of its diameter upon compression in a longitudinal direction or a limited decrease in diameter upon elongation of the braided hollow rope. However, woven is defined herein, including in the claims, to include sheeted circular material of a matted type which may not technically fit the classical definition of a woven rope.

The present invention is particularly suited to the insertion of such a flexible hollow rope material into a hole formed by a drill or a reamer. Such a hole may not be round, but may be of other shapes including oval or irregular, particularly when a reamer or drill is provided with a sidewise force during the drilling or reaming operation. However, the present invention provides particular advantages where such material needs to be inserted in a direction into a bore hole formed by such drilling or reaming, as contrasted to being laid into a channel.

The core-paste material utilized herein may be any suitable composite or acrylic material. Such core-paste material is conventionally utilized in forming cores over posts in preparation for crowns. Preferably, such core-paste material is of the autocure type (self-curing automatically without the need for application of light) to ensure that there can be sufficiently rapid and adequate curing within a post in a posthole where the material may not be readily exposable to light.

Figure 2:
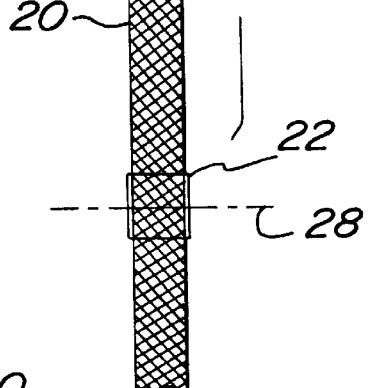
FIG. 2 is an elevation view illustrating a hollow woven (including braided) rope being mounted over a hollow needle attached to a tube cartridge or container for core-paste.

Referring now to FIG. 2, it is shown a woven hollow rope 20, which is preferably comprised of a braided fiberglass. Preferably, woven hollow rope 20 may be silanated or etched and silanated.

In accordance with a preferred embodiment of the present invention, a clear bonding agent or other suitable bonding agent may be applied at 22 which is a predetermined distance from first end 24 of woven hollow rope 20. Preferably, this predetermined distance is selected to comport with the desired length of the post and is of a distance which is less than or equal to the length of the mandrel 26, which is preferably a hollow needle.

After curing of clear bonding agent 22, a cut is made at 28 through the cured bonding agent. This provides a closed end as may be best seen in FIG. 3 at 30. The first or upper end 24 is allowed to fray slightly which aids in the mounting of the woven hollow rope 20 over mandrel or hollow needle 26. In a presently preferred embodiment, hollow needle 26 is attached to a tube cartridge or container 32 which may be loaded with core-paste material for subsequent forcing through hollow needle 26. The core-paste material may be forced from tube cartridge or container 32 through the hollow center of needle 26 by a syringe or any other suitable device or procedure.

Figure 3:
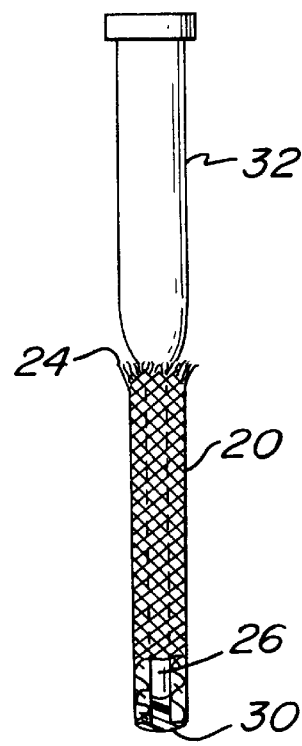
FIG. 3 is an elevation view of the woven (including braided) hollow rope mounted over the hollow needle.

As shown in FIG. 3, woven hollow rope 20 is mounted over hollow needle 26 with closed end 30 adjacent or juxtaposed the distal end of hollow needle 26.

Figure 4:
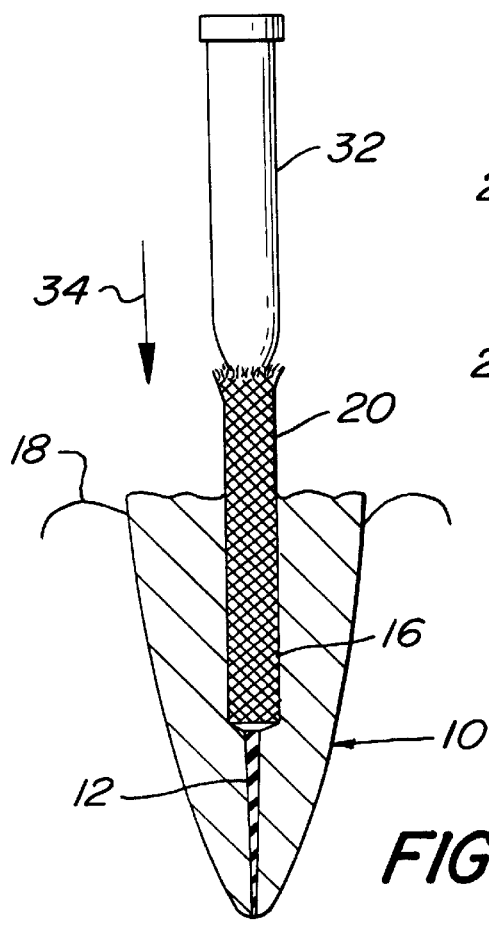
FIG. 4 is an elevation view, partially in cross-section, of the hollow rope being inserted into a post hole of a tooth as shown in FIG. 1.

As may be best seen in FIG. 4, woven hollow rope 20 is inserted into post hole 16 in the direction of arrow 34 by the use of hollow needle 26. In this manner, woven hollow rope 20 may be maintained in a sufficiently rigid condition to force it into post hole 16.

Referring now to FIG. 5, hollow needle 26 may be withdrawn while simultaneously injecting core-paste 36 into woven hollow rope 20. The core-paste being pressed into woven hollow rope 20 helps to maintain woven hollow rope 20 in place within bore hole or post hole 16. The application of the core-post from the inside in this manner further provides the advantages of wetting the fibers and fabric of woven hollow rope 20 from the inside out and expanding the fabric of woven hollow rope 20 tightly against the inner surface of post hole 16. Further, the core-paste will be forced between the fibers or yarns of which the woven (braided) hollow rope 20 is comprised forming a secure bond to the inner surface of post hole 16, and therefore a secure bond to tooth 10.

Referring now to FIG. 6, there is shown a reinforced post 38 which is formed from the combination of woven hollow rope 20 and core-paste 36 after hollow needle 26 has been fully withdrawn.

Referring to FIG. 7, there is shown a core 40 which has been formed over post 38. The core 40 may be formed in substantially the conventional manner utilized in forming cores over metal posts. However, advantages of the method of the present invention include the fact that post 38 is comprised of the same core-paste material, and accordingly, there is a uniformity of material throughout. This is illustrated in FIG. 7 wherein the expansion of core paste material 36 shown at the top of post 38 is indistinguishable from the remainder of the core material.

In accordance with well known procedures, core 40 would be suitably shaped and prepared for a crown and a crown would be attached over core 40.

Referring now to FIG. 8, there is shown another embodiment of the present invention wherein the mandrel 42 utilized for insertion of the woven hollow rope 44 into a bore hole or post-hole 46 in a tooth 48 would be provided with retaining means such as slanted barbs or projections 50 thereby enabling the hollow woven rope to be inserted into the post hole 46 without first providing a closed end on woven hollow rope 44. In the method illustrated in FIG. 8, the woven hollow rope 44 would be applied over mandrel 42 outside of the tooth in the direction of arrow 52. The hollow woven rope 44 would then slide over the barbs 50. Barbs 50, because of their direction of slant, would hold hollow woven rope 44 in place while it is being inserted into post hole 46.

Once the hollow woven rope was inserted into post hole or bore hole 46, mandrel 42 may be withdrawn in a direction opposite to that of arrow 52 leaving the hollow woven rope in place. Mandrel 42 may be either a solid bar or rod or a hollow needle. If mandrel 42 were a hollow needle, the core-paste material could be injected into the center of hollow woven rope 44 prior to removal of mandrel 42. Also, if mandrel 42 were a hollow needle, the upper end of the hollow needle 42 would be inserted into a tube cartridge or container similar to tube cartridge or container 32 after the hollow woven rope 44 was placed on the mandrel. If mandrel 42 were a solid bar or rod, then, after removal of mandrel 42, a hollow needle would be inserted into the center of hollow woven rope for the injection of the core-paste material.

Referring now to FIG. 9, there is shown a variation of the method in accordance with the present invention wherein a plurality of posts 60 and 62 (attachment posts) may be utilized to support a pontic or artificial tooth 64.

As illustrated in FIG. 9, spaced teeth or molars 66 and 68 are shown in which bore holes or post holes 70, 72, 74 and 76 are formed. Posts 60 and 62 would be formed in accordance with the method as described more fully with respect to the preceding figures. Additionally, although posts are not shown in post-holes 74 and 76, posts would also be formed in post holes 74 and 76. Therefore, pontic 64 would be attached and supported by four posts. However, it is understood that more or less posts may be utilized in the practicing of such a method.

In continuing to refer to FIG. 9, the free ends 80 and 82 may be bonded together by a composite 78 prior to the formation of the pontic. This may stabilize the free ends, particularly before the formation of the pontic 64. Alternatively, free ends 80 and 82 need not be bonded together in this manner as the formation of pontic 64 thereon will achieve this purpose.

Referring now to FIG. 10, there is shown another embodiment of the present invention wherein a single post may be anchored in two teeth 90 and 92 which may be separated by a space 94 of a missing tooth. FIGS. 9 and 10 are merely examples of the various applications in which posts may be formed in accordance with the methods of the present invention.

Referring to FIG. 10 more particularly, tooth 90 is illustrated, by way of example, as being a broken off tooth in which one end of post 100 may be inserted into a post or bore hole formed in a tooth similar to the procedures discussed and illustrated with respect to FIGS. 1 through 8. Alternatively, post 100 may be inserted into tooth 90 by utilizing a mandrel in the form of a hollow needle piercing through the sidewall of woven hollow rope 100 to insert the woven hollow rope into the post or bore hole formed in tooth 90 and to inject core-paste material. The mandrel or hollow needle may be inserted through the sidewall of the woven hollow rope 100 by either making a small slit in the sidewall or by inserting the mandrel or needle between the fibers or yarns which comprise the woven hollow rope. As illustrated in FIG. 10, mandrel 102 may then be used to insert the second end of post 100 formed of a woven hollow rope into post hole 104. End 106 of woven (braided) hollow rope 96 may be closed to aid in the insertion process. Alternatively, mandrel 102 may be barbed, but preferably, mandrel 102 would be hollow so that the end of the rope could be inserted into the post hole and simultaneously filled. End 106 could be closed by the application of clear bonding material at the same time that the other end of the hollow rope is closed prior to insertion into tooth 90, or, alternatively, end 106 could be closed by applying a clear bonding material to end 106 after insertion of the first free end into tooth 90.

As a specific example of one application of the present invention, a patient of mine presented requiring a crown on her maxillary right cuspid, which had previously completed endodontic treatment. After suitable examination and removal of any decay, it was determined that the tooth was restorable, but needed a dental post for proper restoration.

An appropriate size post hole reamer was used to remove the gutta percha to create a uniform channel one-half to two-thirds the length of the tooth. The internal walls of the post hole, as well as the remaining coronal tooth structure, were etched with 37% phosphoric acid for 15 seconds and flushed with water. A combination of air-spray and absorbent endodontic paper points were used to remove excess moisture. A universal dental adhesive was then placed on the etched surfaces, using air-spray and endodontic paper points to remove excess resin. A small bead of clear bonding resin (1–2 mm.) was placed next to the end-binder on a piece of GlasSpan rope and light-cured. GlasSpan rope is commercially available from GlasSpan Inc., 101 J. R. Thomas Drive, Exton, Pa. 19341. The hollow GlasSpan rope was then cut directly through the cured resin to produce a clean working end. A second cut was made in the hollow GlasSpan rope at a length matching that of the needle tip on the Centrix tube cartridge. Centrix tube cartridges are available from Centrix, Inc. of Shelton, Conn. Clear bonding resin was not placed on the GlasSpan prior to making the second cut, allowing that end to unravel slightly. This facilitated loading of the GlasSpan rope onto the needle tip. The previously cut end remains sealed with resin as a stop for the needle tip. The needle tip was completely inserted into the hollow end of the GlasSpan rope. The entire surface of the hollow GlasSpan rope was coated with clear bonding resin, which was not cured at this time. An autocured core-paste material, thin enough to pass through the needle tip, was mixed and filled through the back end of the Centrix tube cartridge. The cartridge was plugged and loaded into a Centrix syringe. The needle tip with the GlasSpan was then inserted to the base of the post hole. The core-paste was injected as the needle tip was slowly withdrawn from the post hole. The force of the core-paste leaving the needle tip allowed the material to extrude between the fibers of the GlasSpan rope and fill the entire post hole to the sidewalls. The hollow GlasSpan rope remained firmly in the canal as the needle tip was withdrawn. The GlasSpan extending from the post hole and the remaining coronal tooth structure were covered with core-paste, which was then allowed to cure. The fiber reinforced core material was prepared to receive a crown utilizing conventional diamonds in a high-speed handpiece.

It will be apparent to those skilled in the art that various other applications and modifications of the method of the present invention of utilizing woven hollow rope, preferably in the form of braided hollow rope, to form reinforced posts in teeth for various dental applications that core-paste material may be any suitable composite or acrylic material.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. A method of producing a post for use in restoring or stabilizing one or more teeth, comprising:

creating a hole in a tooth;

obtaining a woven hollow rope;

mounting said hollow rope over a mandrel;

inserting said rope on said mandrel into said hole; and withdrawing said mandrel and filling said hollow rope with a core-paste material.

2. A method in accordance with claim 1 including the step of applying a bonding agent to a portion of said woven hollow rope, allowing said bonding to cure and cutting said woven hollow rope in the area where said bonding agent was applied producing a closed end.

3. A method in accordance with claim 1 wherein said obtaining step includes the step of obtaining a woven hollow rope in the form of a braid.

4. A method in accordance with claim 1 wherein said mounting step includes mounting said hollow rope over a mandrel in the form of a hollow needle.

5. A method step in accordance with claim 1 wherein said mounting step includes the step of mounting said hollow rope over a mandrel in the form of a hollow needle attached to a syringe.

6. A method in accordance with claim 1 wherein said mounting step includes the step of mounting said hollow rope over a mandrel provided with retaining means on its surface for retaining said hollow rope in position on said mandrel while inserting said rope on said mandrel into said hole.

7. A method in accordance with claim 1 including the step of forming a core over said hollow rope with core-paste material therein.

8. A method in accordance with claim 1 wherein said core-paste material is selected to be of the autocure type.

9. A method in accordance with claim 1 wherein said woven hollow rope is constructed from a ceramic fiber material.

10. A method in accordance with claim 1 wherein said woven hollow rope is constructed of a glass fiber material.

11. A method in accordance with claim 10 wherein said step of obtaining a woven hollow rope includes the step of obtaining a rope constructed of glass fibers which have been silanated.

12. A method in accordance with claim 10 wherein said step of obtaining a woven hollow rope includes the step of obtaining a rope constructed of glass fibers which have been etched and silanated.

13. A new use for hollow woven rope including the step of inserting said rope into a bore hole in a tooth wherein said hollow woven rope may be filled with a core-paste material to form a dental post.

14. A method of producing a post for use in connection with a root canal procedure, comprising:

reaming gutta percha from the root canal of a tooth and forming an appropriate size post hole in said tooth;

obtaining a woven hollow rope;

applying a bonding agent to said woven hollow rope at a selected location and allowing said bonding agent to cure;

cutting said woven hollow rope within the location where said bonding agent had been applied;

mounting said hollow rope over a hollow needle with said closed end of said hollow rope being juxtaposed at distal end of said hollow needle;

inserting said hollow rope on said hollow needle into said hole in said tooth;

applying a core-paste material through said hollow needle and into said hollow rope while simultaneously withdrawing said needle from said hollow rope.

15. A method in accordance with claim 14 wherein said step of obtaining a woven hollow rope includes the step of obtaining a woven hollow rope which is braided.

16. A method in accordance with claim 14 including the step of applying a core-paste material which is of the autocure type.

17. A method in accordance with claim 14 wherein said step of obtaining a woven hollow rope includes the step of obtaining a woven hollow rope comprised of ceramic fibers.

18. A method in accordance with claim 14 wherein said step of obtaining a woven hollow rope includes the step of obtaining a woven hollow rope comprised of glass fibers.

19. A method in accordance with claim 14 wherein said step of obtaining a woven hollow rope includes the step of obtaining a woven hollow rope comprised of silanated glass fibers.

20. A method in accordance with claim 14 wherein said step of obtaining a woven hollow rope includes the step of obtaining a woven hollow rope comprised of etched and silanated glass fibers.

21. A method in accordance with claim 14 including the further step of forming a core over said post by applying a core-paste material over said post.

22. A method of producing a post for support or attachment of another dental structure to a tooth, comprising the steps of:
   creating a bore hole in said tooth;
   obtaining a woven hollow rope;
   applying a bonding agent to a portion of said woven hollow rope at a predetermined location from a first end of said rope;
   allowing said bonding agent to cure and cutting said woven hollow rope in the area where said bonding agent was applied to form a closed end;
   mounting said hollow rope over a hollow needle having a proximal end and a distal end, said closed end of said rope being juxtaposed said distal end of said needle;
   inserting said rope on said hollow needle into said hole; and
   applying a core-paste material through said hollow needle and into said hollow rope, filling said hollow rope while said needle is being withdrawn from said hollow rope.

23. A method in accordance with claim 22 wherein said step of obtaining a woven hollow rope includes the step of obtaining a woven hollow rope which is braided.

24. A method in accordance with claim 22 wherein said step of applying a core-paste material includes the step of applying a core-paste material which is of the autocure type.

25. A method in accordance with claim 22 wherein said step of obtaining a woven hollow rope includes the step of obtaining a woven hollow rope constructed of ceramic fibers.

26. A method in accordance with claim 22 wherein said step of obtaining a woven hollow rope includes the step of obtaining a woven hollow rope constructed of glass fibers.

27. A method in accordance with claim 22 wherein said step of obtaining a woven hollow rope includes the step of obtaining a woven hollow rope constructed of silanated glass fibers.

28. A method in accordance with claim 22 wherein said step of obtaining a woven hollow rope includes the step of obtaining a woven hollow rope constructed of etched and silanated glass fibers.

29. A method of producing a bridge having posts anchored in two separated teeth, including producing a post as set forth in accordance with the steps set forth in claim 22 in each of said two separated teeth, and bonding together the exposed ends of said posts.

30. A method of producing a bridge in accordance with claim 29 including the step of using a composite resin to bond together said exposed ends of said posts.

31. A method of producing a bridge having posts anchored in two separated teeth, comprising the steps of:
   creating a first bore hole in a first of said two separated teeth;
   creating a second bore hole in a second tooth of two separated teeth;
   obtaining a woven hollow rope;
   applying a bonding agent to a portion of said woven hollow rope at a predetermined location from a first end of said rope;
   allowing said bonding agent to cure and cutting said woven hollow rope in the area where said bonding agent was applied to form a closed end;
   mounting said hollow rope over a hollow needle having a proximal and a distal end, said closed end of said rope where said bonding agent was applied being juxtaposed at distal end of said needle;
   inserting said rope on said hollow needle into said first hole and said first tooth;
   applying a core-paste material through said hollow needle and into a portion of said hollow rope, filling a portion of said hollow rope from said closed end back while said needle is being withdrawn from said hollow rope;
   inserting said needle through a side of an intermediate portion of said hollow rope wherein said hollow needle may be utilized to insert said first end of said rope into said second hole in said second tooth; and
   applying a core-paste material through said hollow needle and into said hollow rope, filling said hollow rope from said second end backward while said needle is being withdrawn from said hollow rope.

32. A method in accordance with claim 31 wherein said step of obtaining a woven hollow rope includes the step of obtaining a woven hollow rope which is braided.

33. A method in accordance with claim 31 wherein said step of applying a core-paste material includes the step of applying a core-paste material which is of the autocure type.

34. A method in accordance with claim 31 wherein said step of obtaining a woven hollow rope includes the step of obtaining a woven hollow rope constructed of ceramic fibers.

35. A method in accordance with claim 31 wherein said step of obtaining a woven hollow rope includes the step of obtaining a woven hollow rope constructed of glass fibers.

36. A method in accordance with claim 31 wherein said step of obtaining a woven hollow rope includes the step of obtaining a woven hollow rope constructed of silanated glass fibers.

37. A method in accordance with claim 31 wherein said step of obtaining a woven hollow rope includes the step of obtaining a woven hollow rope constructed of etched and silanated glass fibers.

38. A method in accordance with claim 31 including the step of applying a bonding agent to a second portion of said woven hollow rope at a predetermined location which is a predetermined distance from said first predetermined location, allowing said bonding agent to cure and cutting said woven hollow rope in the area where said bonding agent was secondly applied to form a second closed end.

39. A new use for hollow woven rope in the form of hollow braided rope including the step of inserting said hollow rope into a bore hole in a tooth wherein said hollow braided rope may be filled with a core-paste material to form a dental post.

40. A method of wetting a reinforcing structure with a dental composite or acrylic dental material, comprising the step of injecting the dental composite or acrylic dental material into the center of a hollow woven rope utilized as the reinforcing structure for the composite or acrylic material.

41. A dental post, comprising a woven hollow rope filled with a core-paste.

42. A dental post in accordance with claim 41 wherein said core-paste is a dental composite.

43. A dental post in accordance with claim 41 wherein said core-paste is an acrylic material.

44. A dental post in accordance with claim 41 wherein said core-paste is of the autocure type.

45. A dental post in accordance with claim 41 wherein said woven hollow rope is a braided woven hollow rope.

46. A dental post in accordance with claim 41 wherein said woven hollow rope is constructed of ceramic fibers.

47. A dental post in accordance with claim 41 wherein said hollow rope is comprised of glass fibers.

48. A dental post in accordance with claim 41 wherein said hollow rope is comprised of silanated glass fibers.

49. A dental post in accordance with claim 41 wherein said hollow rope is comprised of etched and silanated glass fibers.

* * * * *